United States Patent [19]

Georgijevic

[11] Patent Number: 5,040,525
[45] Date of Patent: Aug. 20, 1991

[54] UNDERGARMENT DEVICE FOR TREATING HIP DISPLACEMENT AND DISLOCATION

[76] Inventor: Ljubomir Georgijević, Smiljaniceva No 6, 11000 Beograd

[21] Appl. No.: 446,295

[22] Filed: Dec. 4, 1989

[51] Int. Cl.⁵ .......................... A61F 5/02; A61F 5/04
[52] U.S. Cl. .................... 128/78; 128/84 R; 128/DIG. 20
[58] Field of Search .............. 128/868, 872, 873, 869, 128/78, 84, 82, DIG. 20, 87 R; 2/DIG. 3, 78 R, 78 C, DIG. 7; 604/385.1, 378, 390

[56] References Cited

U.S. PATENT DOCUMENTS

| | | | |
|---|---|---|---|
| 2,762,366 | 9/1956 | Huxley | 128/DIG. 20 |
| 2,828,745 | 4/1958 | Deutz | 604/378 |
| 2,880,721 | 4/1959 | Corcoran | 128/DIG. 20 |
| 3,071,133 | 1/1963 | Eisen | 128/DIG. 20 |
| 3,559,648 | 2/1971 | Mason | 604/378 |
| 3,823,712 | 7/1974 | Morel | 128/87 R |
| 3,933,150 | 1/1976 | Kaplan | 128/DIG. 20 |
| 4,039,039 | 8/1977 | Gottfried | 128/87 R |
| 4,055,180 | 10/1977 | Karami | 604/378 |
| 4,559,933 | 12/1985 | Batard | 128/DIG. 20 |
| 4,624,248 | 11/1986 | Poole | 128/87 R |
| 4,703,750 | 11/1987 | Sebastian | 128/DIG. 20 |
| 4,737,994 | 4/1988 | Galton | 2/DIG. 3 |
| 4,850,992 | 7/1989 | Amaral | 604/385.1 |
| 4,870,706 | 10/1989 | Ketcham | 128/DIG. 20 |
| 4,904,252 | 2/1990 | Fitzgerald | 604/385.1 |

Primary Examiner—Danton D. DeMille
Assistant Examiner—Michael Brown
Attorney, Agent, or Firm—Douglas A. Chaikin

[57] ABSTRACT

Disclosed herein is an undergarment device for treating hip displacement and hip dislocation. The device includes a panty member having a first open position generally in the shape of a rectangle and a second position wherein the panty member is wrapped around the hips of a user. The longer sides of the rectangle shape covers the front and back of a user in the second position and the shorter sides cover the sides of a user and extend past the hips to the legs in the second position. Each of the longer and shorter sides intersect at vaulted recesses defining openings for a user's legs in the second position. The panty member includes structure for fastening the device to itself. The panty member further includes a valve on one of the layers for allowing fluid, such as air, to be injected between the layers for spacing apart the layers. Upon placing the device around the hips of a user and fastening the device to itself and injecting fluid between the layers, the hips of the user are supported by the device.

18 Claims, 3 Drawing Sheets

UNDERGARMENT DEVICE FOR TREATING HIP DISPLACEMENT AND DISLOCATION

RELATED APPLICATIONS

This application is the U.S. equivalent of the Yugoslavian Application, filed December 2, 1988 as Ser. No. P-2195/88 and published as a granted patent June 14, 1989, registration number 2195/88/3.

BACKGROUND OF THE INVENTION

1. Field of the Invention

This invention relates to medical devices and more particularly to orthopedic devices in the field of corrective corsets.

2. Previous Art

Perhaps one of the one devastating and widespread genetic defects is the displacement and dislocation of hips of newborns. Orthopedic surgeons as well as others in the medical field have long strived to prevent and treat this devastating hereditary problem. The hip joint is the epicenter of virtually all natural locomotion. The hip joint is quite complex. In order for the hip joint to operate properly, the bulb of the thighbone must fit properly within the hip joint (patella) with the correct acetabulum ratio. Additionally, the alignment of the thighbone and hip joint may have only a minimum deviation from the ideal to work properly.

Man's transition from the quadrupedal into the upright posture caused a rotation of the stresses in the skeletal structure. It was the hip joint of the skeletal structure which was primarily responsible for adapting to these new stresses. The quadrupedal ratio has changed with time as man continued his upright position. The perpendicular ratio of the joints was adapted, including the inclination of the acetabulum—the patella.

The footing centers of the hip bone structures are very small and even small deviations from the ideal causes a pathological condition. A person with such small deviations may suffer from hip displacement and hip dislocation depending on the orientation of his thigh bone with the patella. The orientations of the bone structure are hereditary and the dominant trait is to have deviations within acceptable limits for locomotion.

Sometimes an infant is born with displacement of the hip with a less developed patella and with a disturbed ideal ratio of the bone structures, e.g. an enlarged bulb and neck of the thighbone. Dislocation of the hips will occur later when an infant is born with such a condition. Thus, even an infant born with only a displacement and having the above condition will have a high risk of hip dislocation because the bulb of the thighbone may easily slip out the patella. The dislocation of the hips will be further encouraged in such an infant as his muscles grow. The muscles will strengthen and exert increasingly greater force on the thighbone, tending to move the bulb of the thighbone out the patella.

In order to have the best chance at correcting the condition described above, an infant with such a condition should be treated immediately. Each passing day from birth lessens the probability that treatment will correct the condition. Therefore, any corrective device should be designed for the new born as well as the older infant and even toddler to be optimum.

Various splints are currently being used with infants and older children, usually beginning when the infant is four months old. Barlow's splint is an "X" shaped splint, made from an aluminum sheet. The sheet is adjusted so that the child is put with its back against the middle of the sheet and then bent downward over the shoulders and collarbones and breasts of the infant. Straps are fitted around the thorax of the infant for further support. The lower parts of the "X" are wrapped around the legs that are bent in the hips and knees. This device must be very carefully adjusted with great attention paid to the thorax area, which if improperly adjusted, can choke the infant. Additionally, the lower "X" section may squeeze or even damage the delicate skin of a new born.

Von Rosen's splint is similarly made from aluminum which is easily bent. This splint is made in the form of the letter "H". This splint fits around the infant in a similar way as Barlow and similarly has the same dangers. Additionally, this type of device renders the infant virtually without any movement during use. And, therefore can cause aseptic necrosis of the thighbone bulb.

Canvas panties are plentiful, for example Waikert's "Niva" which includes soft and hard inserts. These type of panties attempt to direct the bulb and neck of the thighbone towards the bottom of the patella. In this way it is hoped that the patella will deepen by the pressure of the bulb and neck against the patella.

As the infant grows older, more and more drastic methods are needed, plaster casts such Higenreiner's device, straps such as Pavlik's and cushions such as Puty.

Also other various devices such as Karaikovic, Patent registration No. P-920/79 entitled "Abduction Device for Hips with a Regulator", Tsentralyny, Patent Registration No. P-2533/78, entitled "Device for Mobility Making in the Pelvic and Hip Joint", Trolic et al, Patent Registration No. P-1374/83, entitled "Abduction Walking Device for Healing Congenital and Residual Hip and Legs Disharmony", Mitkovic, Patent Registration No. P-253/85, entitled "The Device for the External Fixing of Long Bones", Mitkovic, Patent Registration No. P-135485, entitled, "Development for External Fixing, Type M 8", Muftic 1366/84, entitled "External Fixer", Muftic, Patent Registration No. P-1247/85 and P-1373/86, Mitkovic, Patent Registration No. P-249/85 entitled "Mini-external Fixer", Muftic, Patent Registration No. P-760/82, entitled "Prosthesis for Healing of Disturbed and Dislocated Joints in Hip" are all known.

However none of the above mentioned devices has solved the problem of every day practice. A successful device should enable an infant to heal and even cure the dislocation and displacement of the hips while allowing every day activity.

SUMMARY OF THE INVENTION

It is an object of this invention to provide a device that assists in the correcting the problem of hip displacement and dislocation.

It is a further object of this invention to provide such a device where the pressure exerted by the device against the hips is adjustable.

It is a further object of this invention to provide such a device that can be effective during waking hours without cutting off normal circulation.

In accordance with the above objects and those that will be mentioned and will become apparent below, the device according to this invention is an undergarment for treating hip displacement and hip dislocation, comprising:

a flexible panty member having a first layer and a second layer, the layers being sealed and made from impermeable material, the panty member including means for fastening the device to itself and the panty member including valve means on one of the layers for allowing fluid to be injected between the layers for spacing apart the layers, whereby upon placing the device around the hips of a user and fastening the device to itself and injecting fluid between the layers, the hips of the user are supported by the device.

In another embodiment, the undergarment for treating hip displacement and hip dislocation in accordance with this invention, comprises:

a panty member having a first open position generally in the shape of a rectangle and a second position wherein the panty member is wrapped around the hips of a user, the longer sides of the general rectangle shape defining covering for the front and back of a user in the second position and the shorter sides defining covering for the sides of a user and extending past the hips to the legs of a user in the second position, each of the longer and shorter sides intersecting at vaulted recesses defining openings for a user's legs in the second position;

the panty member including means for fastening the device to itself; and the panty member including valve means on one of the layers for allowing fluid to be injected between the layers for spacing apart the layers, whereby upon placing the device around the hips of a user and fastening the device to itself and injecting fluid between the layers, the hips of the user are supported by the device.

And in still another embodiment, the undergarment for treating hip displacement and hip dislocation in accordance with this invention, comprises:

a panty member having a first open position generally in the shape a panty member of a rectangle and a second position wherein the panty member is wrapped around the hips of a user, the panty member having tubular sections of approximately the same diameter extending from one side of the member to the other and each of the tubular sections openly communicating with each other, the longer sides of the general rectangle shape defining covering for the front and back of a user in the second position and the shorter sides defining covering for the sides of a user and extending past the hips to the legs of a user in the second position, each of the longer and shorter sides intersecting at vaulted recesses defining openings for a user's legs in the second position;

the panty member including means for fastening the device to itself; and the panty member including valve means on one of the layers for allowing fluid to be injected between the layers for spacing apart the layers, whereby upon placing the device around the hips of a user and fastening the device to itself and injecting fluid between the layers, the hips of the user are supported by the device.

All of the above, include a preferred embodiment which can be filled with air making the device a pneumatic panty. Additionally, the valve used in the preferred embodiment is a two way valve giving the user the ability to vary the amount of the air in the device. Consequentially the amount of pressure exerted by the device on the thigh bone and patella is variable.

In all of the preferred embodiments, the user is allowed virtually unlimited movements thereby avoiding muscle atrophy.

It is an advantage of this invention to provide the user with a device that allows use without compromising the user's circulation system.

It is an additional advantage of this invention to provide a device that can be worn during the waking or sleeping hours.

It is an additional advantage of this invention to provide a device where the pressure exerted by the device on the user's hips can be increased during non-waking hours.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

Figure 3:
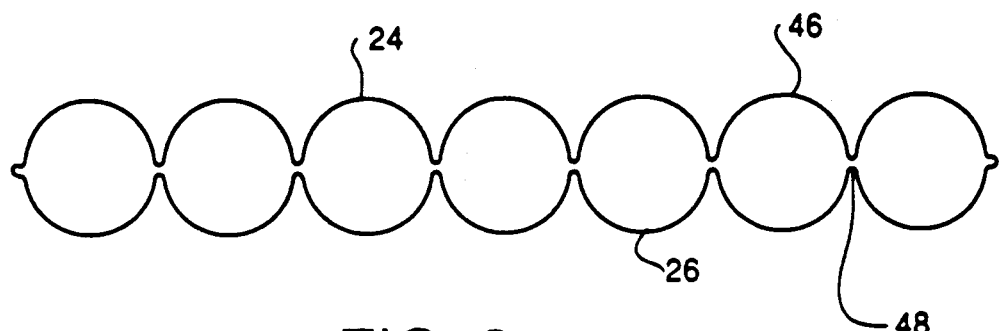
FIG. 3 is a cross-sectional view of the device of FIG. 1 showing the tubular sections.
Figure 4:
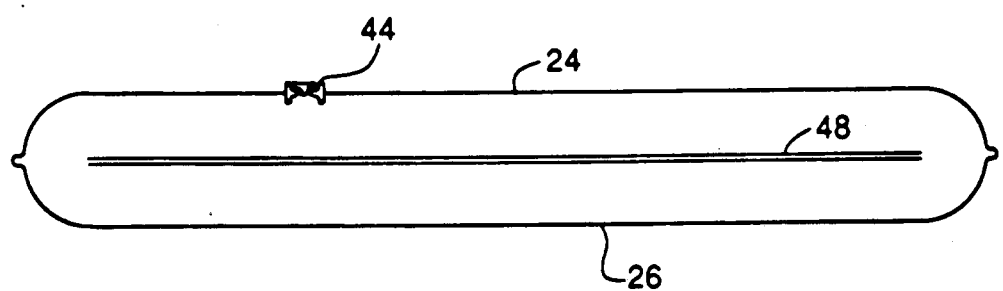
FIG. 4 is a cross-sectional view of one of the tubular sections of FIG. 3.

The invention will now be described with respect to FIGS. 1 through 4, which illustrate the undergarment device indicated generally by the numeral 20. The device 20 includes a panty member 22 having first and second layers, 24 and 26, respectively, which are best seen in FIGS. 3 and 4.

The panty member 22 has a general rectangular shape with opposed longer sides 28 and shorter sides 30. The panty member 22 is made from a flexible and impermeable material. The longer sides 28 and shorter sides 30 are parallel pairs and are perpendicular to each other. The sides 28 and 30 intersect each other at vaulted recesses 32 and 34. The sides 28 cover the user's back and front, while the sides 30 cover the user's sides and hips and extend to the tops of the user's legs as seen most clearly in FIG. 1.

Fastening members 36, 38, 40 and 42 are provided on the panty member 22 for connecting the panty member 22 to itself. Fastening members 36 and 38 are male velcro members and connect with fastening members 40 and 42, respectively, which are female velcro fastening members.

It will be appreciate that various types of fastening members can be chosen and velcro is used as one form because it is reusable and easily removable and easily connectable. Other types of fastening members such as the kind currently used in disposable diapers could be used and would be effective on a one time basis and are within the spirit and scope of this invention.

The male fastening members 36 and 38 extend into the vaulted recesses 32 are approximately perpendicular to each other. In the preferred embodiment, the male fastening members 36 and 38 extend at least part way into the vaulted recesses 32 and approximately half of their length and are spaced apart but adjacent each other.

The female fastening members 40 and 42 are affixed to the panty member 22 adjacent the vaulted recesses 34. The female fastening members 40 and 42 are positioned for compatible engagement with the male fastening members 36 and 38 with their longitudinal center lines approximately perpendicular to each other.

A valve 44 is provided on the panty member 22 for pumping fluid into and allowing fluid out of the panty member 22. It will be appreciated that the fluid used in the preferred embodiment is air but other fluids in including liquids could also be used within the spirit and scope of the invention herein.

Figure 1:
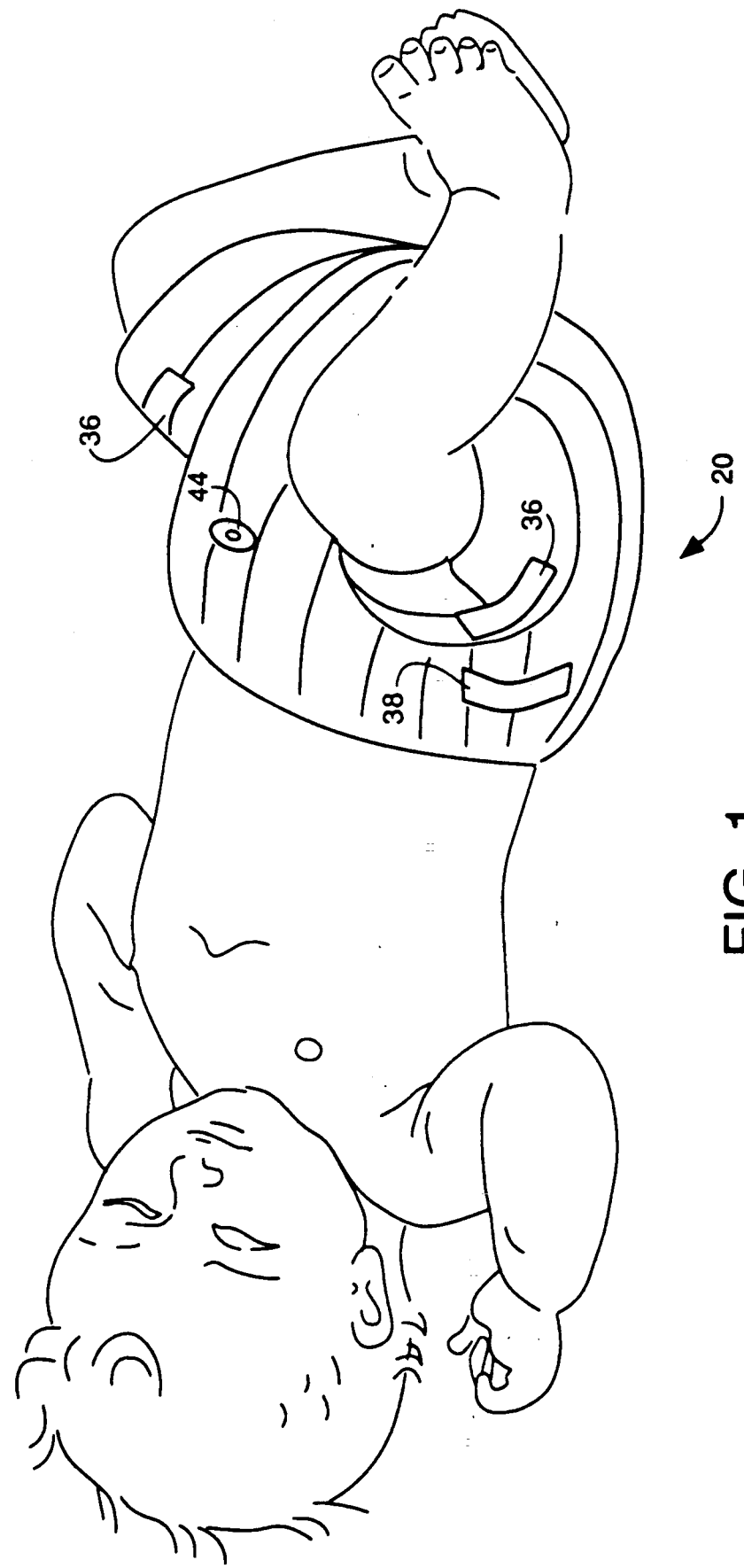
FIG. 1 is an elevated perspective view of the device in accordance with this invention wrapped around the hips of an infant.
Figure 2:
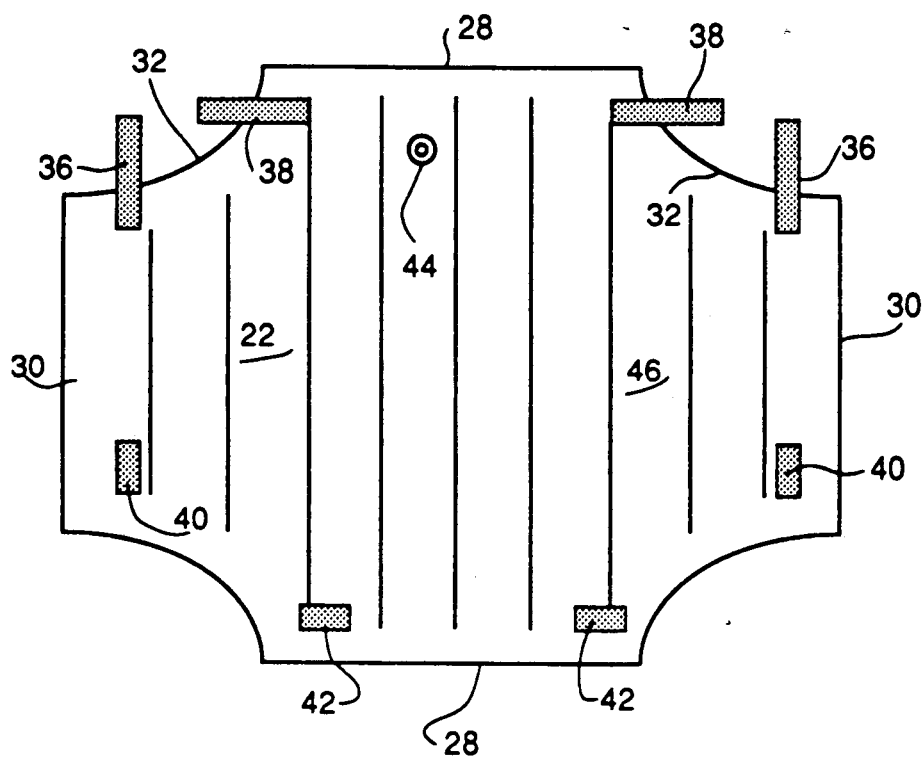
FIG. 2 is a front plan view of the device of FIG. 1 in the open position.

As shown particularly in FIGS. 3 and 4, the panty member 22 is divided into a plurality of tubular sections 46. The tubular sections 46 extend from one side of the panty member 22 to the other and in the preferred embodiment, the tubular sections extend between the longer sides 28 as seen in FIG. 1. This makes the tubular sections 46 of unequal lengths when filled with air. Between each of the tubular sections 46, there is a narrow portion 48. The narrow portions 48 are parallel to each other.

IN USE

The device 20 can be wrapped around the user as shown in FIG. 1 by placing the user on the panty member 22 in much the same manner as a diaper is wrapped around an infant. The male fastening members 36 and 38 are then secured to the female fastening members 40 and 42, respectively. Air (or other fluid as appropriate) is injected into the panty member 22 through the valve 44 until the desired pressure level is reached. The ability to pump air in until the desired pressure is reached allows the hip to take the proper relationship with the thigh bone and the lower extremities. Thus, an ideal position can be achieved for a variety of different users.

To remove the device 20 from the user, the air is expelled through the valve 44 and the fastening members 36, 38, 40 and 42 are unfastened. The panty member 22 is then removed and can be cleaned and dried as appropriate.

The correct placement of the hips is required to afford maximum effectiveness in using the device 20. In order that the bulb and neck of the thighbone are directed to the most ideal position in a case where the user has aseptic necrosis, the lower extremities bent in the hips must make an angle of less than 90°. The legs of the user should be spread apart approximately 60° in relation to the imaginary median line from the user's head to pubic bone. In this preferred position the user gets the maximum effectiveness of the device 20 and there are no harmful side effects from lack of circulation of the blood supply to the user's lower extremities. Thus, the ideal position of the thighbone and hip joint (patella) can be achieved using this device without cutting off normal blood circulation.

The full effect of the device 22 is achieved when the user is asleep and pressure and be increased and the user's position of thigh bone and patella are relatively stationary.

It is believed that virtually all of the affects of hip displacement and hip dislocation can be eliminated if the device 20 is used immediately after the birth of the user. Additionally, after proper instruction, it is not necessary for the user's care provider to be a professionally trained person. Anyone capable of caring for a infant or small child can easily learn to use the device 20 with great effectiveness.

While the foregoing detailed description has described several embodiments of the undergarment device for treating hip displacement and hip dislocation in accordance with this invention, it is to be understood that the above description is illustrative only and not limiting of the disclosed invention. Particularly, various types of impermeable material can be use and shapes other than rectangular shapes may be appropriate. It will be appreciated that while the user's are expected to be infants or small children, the device may also be used by others within the scope and spirit of this invention. Thus, the invention is to be limited only by the claims as set forth below.

What is claimed is:

1. An undergarment device for treating hip displacement and hip dislocation, comprising:
   a single piece panty member having a first layer and a second layer, the first and second layers being sealed and made from impermeable material,
   the panty member including means for fastening the device to itself; and
   the panty member including valve means on one of the layers for allowing fluid to be injected between the layers for spacing apart the layers,
   whereby upon placing the device around the hips of a user and fastening the device to itself and injecting fluid between the layers, the hips of the user are supported by the device.

2. An undergarment device as set forth in claim 1, wherein the panty member is sized and shaped to fit around the hips of an infant or small child.

3. An undergarment device as set forth in claim 1, wherein the valve allows the ingress and egress of fluid between the layers.

4. An undergarment device for treating hip displacement and hip dislocation, comprising:
   a panty member having a first open position generally in the shape of a rectangle and a second position wherein the panty member is wrapped around the hips of a user, the longer sides of the general rectangle shape defining covering for the front and back of a user in the second position and the shorter sides defining covering for the sides of a user and extending past the hips to the legs of a user in the second position, each of the longer and shorter sides intersecting at vaulted recesses defining openings for a user's legs in the second position;
   the panty member including means for fastening the device to itself; and
   the panty member including valve means on one of the layers for allowing fluid to be injected between the layers for spacing apart the layers,
   whereby upon placing the device around the hips of a user and fastening the device to itself and injecting fluid between the layers, the hips of the user are supported by the device.

5. An undergarment device as set forth in claim 4, wherein the panty member comprises a plurality of side-by-side tubular sections extending from one side of the panty member to the other.

6. An undergarment device as set forth in claim 5, wherein the tubular sections are of unequal length.

7. An undergarment device as set forth in claim 6, wherein the tubular sections openly communication with each other.

8. An undergarment device as set forth in claim 6, wherein each of the tubular sections are of the same diameter.

9. An undergarment device as set forth in claim 5, wherein the tubular sections extend between the longer sides of the panty member.

10. An undergarment device as set forth in claim 4, wherein the fastening means comprises male and female mating members.

11. An undergarment device as set forth in claim 10, wherein the fastening means includes four male and four female sections position at opposite portions of the vaulted recesses.

12. An undergarment device as set forth in claim 11, wherein the fastening means includes the male sections on that portion of the panty member which is adjacent that portion which covers the back and the back of the hips and legs and the female sections affixed to the panty member portion which covers the front and front of the hips.

13. An undergarment device as set forth in claim 12, wherein two of the fastening means male sections are adjacent the same vaulted recess and extend therein and are approximately perpendicular to each other and the other two male sections on similarly positioned on an opposite vaulted recess.

14. An undergarment device as set forth in claim 13, wherein the female sections of the fastening means are position on adjacent vaulted recesses so that they are compatible with the male sections.

15. An undergarment device as set forth in claim 4, wherein the amount of fluid in the device is variable and therefore in the closed position the panty member exerts a variable pressure against the hips of a user.

16. An undergarment device as set forth in claim 15, wherein the fluid in the device is air.

17. An undergarment device as set forth in claim 4, wherein valve means comprises a two-way valve for allowing fluid in and out.

18. An undergarment device for treating hip displacement and hip dislocation, comprising:

a panty member having a first open position defining generally the shape of a rectangle and a second position wherein the panty member is wrapped around the hips of a user, the panty member having tubular sections of approximately the same diameter extending from one side of the member to the other and each of the tubular sections openly communicating with each other, the longer sides of the general rectangle shape defining covering for the front and back of a user in the second position and the shorter sides defining covering for the sides of a user and extending past the hips to the legs of a user in the second position, each of the longer and shorter sides intersecting at vaulted recesses defining openings for a user's legs in the second position;

the panty member including means for fastening the device to itself; and the panty member including valve means on one of the layers for allowing fluid to be injected between the layers for spacing apart the layers, whereby upon placing the device around the hips of a user and fastening the device to itself and injecting fluid between the layers, the hips of the user are supported by the device.

* * * * *